United States Patent [19]

Kim et al.

[11] Patent Number: 5,554,631
[45] Date of Patent: Sep. 10, 1996

[54] 5-PYRROLYL-6-HALOGENO-2-PYRIDYLMETHYLSULFINYL BENZIMIDAZOLE DERIVATIVES

[75] Inventors: Su U. Kim; Dong Y. Kim, both of Seoul; Gi J. Chung; Sung K. Hong, both of Kyungki-do; Sung J. Park; Sang H. Nam, both of Seoul; Seung M. Lee, Kyunggi-do, all of Rep. of Korea

[73] Assignee: Il-Yang Pharm. Co., Ltd., Seoul, Rep. of Korea

[21] Appl. No.: 408,167

[22] Filed: Mar. 21, 1995

[30] Foreign Application Priority Data

Feb. 12, 1994 [KR] Rep. of Korea .................... 94-32612

[51] Int. Cl.$^6$ .................... C07D 401/12; A61K 31/44
[52] U.S. Cl. .................... 514/338; 546/112; 546/115; 546/194; 546/148; 546/273.7; 544/124; 544/131; 544/364
[58] Field of Search .................... 546/271; 514/338

[56] References Cited

U.S. PATENT DOCUMENTS

| | | | |
|---|---|---|---|
| 4,255,431 | 3/1981 | Junggren et al. | 546/271 |
| 4,337,257 | 6/1982 | Junggren et al. | 546/271 |
| 4,508,905 | 4/1985 | Junggren et al. | 546/271 |
| 4,758,579 | 7/1988 | Kohi et al. | 546/271 |

FOREIGN PATENT DOCUMENTS

| | | |
|---|---|---|
| 5129 | 10/1979 | European Pat. Off. . |
| 268956 | 6/1988 | European Pat. Off. . |
| 2134523 | 8/1994 | United Kingdom . |

OTHER PUBLICATIONS

CA 105:226619, Yano et al. 1986.

*Primary Examiner*—Jane Fan
*Attorney, Agent, or Firm*—Lowe, Price, LeBlanc & Becker

[57] ABSTRACT

The present invention relates to a novel compound 5-pyrrolyl-6-halogeno-2-pyridylmethylsulfinylbenzimidazole derivative having the following formula (I):

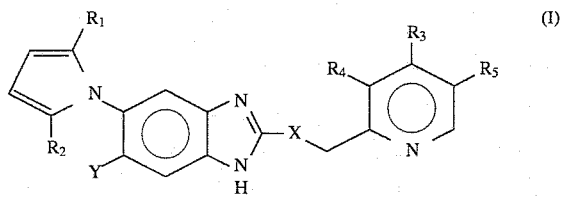

or a pharmaceutically acceptable salt thereof, in which
X represents S, SO or SO$_2$,
Y represents halogen,
$R_1$ and $R_2$ independently from each other represent hydrogen or methyl,
$R_3$ represents hydrogen, $C_1$–$C_8$ alkyl, —SR$_6$, —N(R$_7$)$_2$, or a group of formula —OR$_6$ or —O(CH$_2$)$_m$—Z, wherein
$R_6$ represents $C_1$–$C_4$ alkyl, $C_2$–$C_4$ alkenyl, $C_3$–$C_{10}$ cycloalkyl optionally substituted with $C_1$–$C_4$ alkyl, $C_2$–$C_5$ fluoroalkyl, phenyl optionally substituted with $C_1$–$C_4$ alkyl or benzyl optionally substituted with $C_1$–$C_4$ alkyl,
$R_7$ represents hydrogen or $C_1$–$C_5$ alkyl,
Z represents a group of formula —O(CH$_2$)$_q$—R$_9$ wherein q denotes an integer of 1 to 3, and R$_9$ represents hydrogen,
m represents an integer of 2 to 10, and

4 Claims, No Drawings

5-PYRROLYL-6-HALOGENO-2-PYRIDYLMETHYLSULFINYL BENZIMIDAZOLE DERIVATIVES

BACKGROUND OF THE INVENTION

1. Field of the Invention

The present invention relates to a novel 5-pyrrolyl-6-halogeno-2-pyridylmethylsulfinylbenzimidazole derivative which is useful as an agent for prophylaxis and treatment of gastric and duodenal ulcers. More specifically, the present invention relates to a novel 5-pyrrolyl-6-halogeno-2-pyridylmethylsulfinylbenzimidazole derivative represented by the following general formula (I):

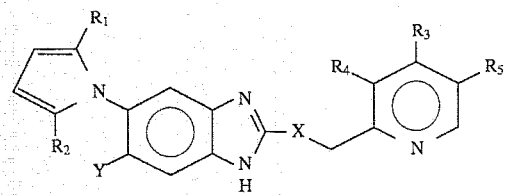

and a pharmaceutically acceptable salt thereof, in which

X represents S, SO or $SO_2$,

Y represents halogen, $R_1$ and $R_2$ independently from each other represent hydrogen or alkyl, $R_3$ represents hydrogen, $C_1$-$C_8$ alkyl, —$SR_6$, —$N(R_7)hd 2$, 1-piperidinyl, 4-morpholinyl, 4-methylpiperazin-1-yl, 1-pyrrolidinyl, or a group of formula —$OR_6$ or —$O(CH_2)_m$—Z, wherein represents $C_1$-$C_4$ alkyl, $C_2$-$C_4$ alkenyl, optionally substituted $C_3$-$C_{10}$ cycloalkyl, $c_2$-$C_5$ fluoroalkyl, or phenyl or benzyl, each of which is independently substituted with one or more halogen or $C_1$-$C_4$ alkyl or alkoxy optionally substituted with halogen, $R_7$ represents hydrogen or $C_1$-$C_5$ alkyl, Z represents a group of formula —$O(CH_2)_p$—$OR_8$, —$O(CH_2)_q$—$R_9$ or —$O(CH_2)_r O(CH_2)_s$—$OR_{10}$, wherein p and q independently from each other denote an integer of 1 to 3, r and s independently from each other denote an integer of 1 to 5, $R_8$ represents hydrogen, lower alkyl, aryl or aralkyl, $R_9$ represents hydrogen, alkoxycarbonyl, aryl or heteroaryl, and $R_{10}$ represents hydrogen or lower alkyl, m represents an integer of 2 to 10, and $R_4$ and $R_5$ independently from each other represent hydrogen or $C_1$-$C_5$ alkyl, or when $R_4$ and $R_5$ together with the carbon atoms adjacent to pyridine ring form a ring, $R_4$ and $R_3$ or $R_3$ and $R_5$ represent —CH=CH—CH=CH—, —$O(CH_2)_n$—, —$O(CH_2)_n O$—, —$CH_2(CH_2)_n$— or —OCH=CH—, wherein n denotes an integer of 1 to 4.

The present invention also relates to a process for preparation of the compound of formula (I), as defined above, and a pharmaceutical composition for prophylaxis and treatment of gastric and duodenal ulcers which contains the compound of formula (I) as an active ingredient.

2. Background Art

Gastric and duodenal ulcers are a gastrointestinal disease caused by various factors such as mental stress, dietary habit, intake of irritable food, and the like, and occur mainly in lower esophagus, stomach or duodenum. In addition, when the gastric membrane is present in small intestine, the ulcers caused by gastric juice secreted therefrom may very rarely occur in small intestine. The cause of peptic ulcers can be generally classified into two cases, that is, one is the strengthening of an offence factor such as gastric acid or pepsin and the other is the weakening of a defense factor against such offence factor. Generally, it has been known that the main cause of duodenal ulcer is the strengthening of an offence factor and the gastric ulcer is mainly caused by the weakening of a defense factor, although the cause of gastric ulcers is somewhat varied depending on the attacked site.

Currently, therapeutic agents which have been commonly used for treatment of the peptic ulcers includes, for example, ant-acids for neutralizing gastric acid, anti-pepsin agents, agents for protecting the gastric mucous membrane, anticholinergic agents for inhibiting gastric secretion, parasympatholytic agents, $H_2$-receptor antagonists, proton pump inhibitors, and the like. At the present time, since it has been disclosed that antacids and CNS-acting anti-ulcer agents provide only a unsatisfactory therapeutic effect and may cause adverse effects when they are administered for a long period, the use of $H_2$-receptor antagonists as agents for treating gastric and duodenal ulcers through a new acting mechanism has increased.

In addition, recently 5-methoxy-2-[[(4-methoxy-3,5-dimethyl -2-pyridinyl)methyl]sulfinyl]-1H-benzimidazole (Generic name: Omeprazole) having the following formula (A) has been developed and demonstrated as a good anti-ulcer agent having a superior effect over conventional $H_2$-receptor antagonists such as cimetidine, famotidine, ranitidine, nizatidine, roxatidine, and the like (see, U.S. patent specification Nos. 4,255,431, 4,337,257, 4,508,905 and 4,758,579, British Patent No. 2,134,523, European Patent Nos. 0,005,129 and 0,268,956). In view of the acting mechanism, contrary to conventional $H_2$-receptor antagonists, Omeprazole is a specific proton pump inhibitor which blocks the proton pump of $H^+$, $K^+$-ATPase present in the gastric mucous membrane to inhibit the gastric secretion at the final stage. In addition, Omeprazole has also an advantage of prolonged duration in comparison with conventional anti-ulcer agents. Accordingly, Omeprazole is widely used in various types of formulations.

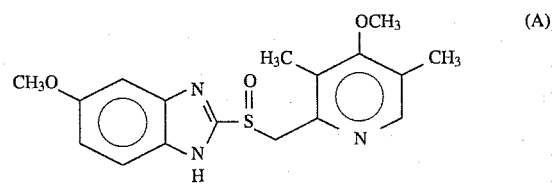

Thus, the present inventors have extensively studied for a long time to develop novel anti-ulcer agents which have a benzimidazole structure similar to Omeprazole and exhibit a superior anti-ulcer effect over Omeprazole. As a result, we have synthesized a novel compound having the general formula (I), as defined above, and then identified that the compound of formula (I) has a superior anti-ulcer effect in comparison with Omeprazole. Thus, now we have completed the present invention.

Therefore, it is an object of the present invention to provide a novel 5-pyrrolyl-6-halogeno-2-pyridylmethylsulfinylbenzimidazole derivative having the general formula (I), as defined above, which is useful as an agent for prophylaxis and treatment of gastric and duodenal ulcers.

It is a further object of the present invention to provide a process for preparation of the novel 5-pyrrolyl-6-halogeno-2-pyridylmethylsulfinylbenzimidazole derivative of formula (I).

Further, it is another object of the present invention to provide a pharmaceutical composition for prophylaxis and treatment of gastric and duodenal ulcers, which contains the novel 5-pyrrolyl-6-halogeno-2-pyridylmethylsulfinylbenzimidazole derivative of formula (I) as an active ingredient.

The foregoing has outlined some of the more pertinent objects of the present invention. These objects should be construed to be merely illustrative of some of the more pertinent features and applications of the invention. Other many beneficial results can be obtained by applying the disclosed invention in a different manner or modifying the invention within the scope of the disclosure. Accordingly, other objects and a more thorough understanding of the invention may be had by referring to the summary of invention and the disclosure of invention describing the preferred embodiment, in addition to the scope of the invention defined by the claims.

SUMMARY OF INVENTION

The first object of the present invention is to provide a novel 5-pyrrolyl-6-halogeno-2-pyridylmethylsulfinylbenzimidazole derivative having the following general formula (I):

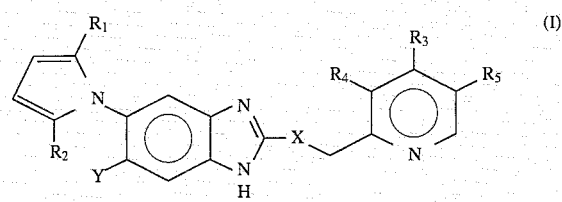

and a pharmaceutically acceptable salt thereof, in which

X represents S, SO or $SO_2$,

Y represents halogen, $R_1$ and $R_2$ independently from each other represent hydrogen or alkyl, $R_3$ represents hydrogen, $C_1$–$C_8$ alkyl, —$SR_6$, —$N(R_7)_2$, 1-piperidinyl, 4-morpholinyl, 4-methylpiperazin-1-yl, 1-pyrrolidinyl, or a group of formula —$OR_6$ or —$O(CH_2)_m$—Z, wherein $R_6$ represents $C_1$–$C_4$ alkyl, $C_2$–$C_4$ alkenyl, optionally substituted $C_3$–$C_{10}$ cycloalkyl, $C_2$–$C_5$ fluoroalkyl, or phenyl or benzyl, each of which is independently substituted with one or more halogen or $C_1$–$C_4$ alkyl or alkoxy optionally substituted with halogen, $R_7$ represents hydrogen or $C_1$–$C_5$ alkyl, Z represents a group of formula —$O(CH_2)_p$—$OR_8$, —$O(CH_2)_q$—$R_9$ or —$O(CH_2)_r O(CH_2)_s$—$OR_{10}$, wherein p and q independently from each other denote an integer of 1 to 3, r and s independently from each other denote an integer of 1 to 5, $R_8$ represents hydrogen, lower alkyl, aryl or aralkyl, $R_9$ represents hydrogen, alkoxycarbonyl, aryl or heteroaryl, and $R_{10}$ represents hydrogen or lower alkyl, m represents an integer of 2 to 10, and $R_4$ and $R_5$ independently from each other represent hydrogen or $C_1$–$C_5$ alkyl, or when $R_4$ and $R_5$ together with the carbon atoms adjacent to pyridine ring form a ring, $R_4$ and $R_3$ or $R_3$ and $R_5$ represent —CH=CH—CH=CH—, —O(CH_2)_n—, —O(CH_2)_nO—, —CH_2(CH_2)_n— or —OCH=CH—, wherein n denotes an integer of 1 to 4.

Another object of the present invention is to provide a process for preparation of the compound of formula (I):

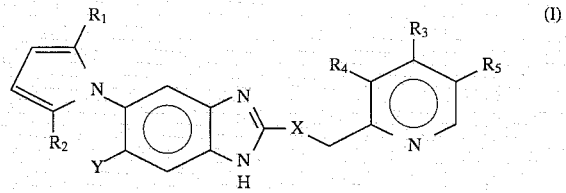

and a salt thereof, wherein X, Y, $R_1$, $R_2$, $R_3$, $R_4$ and $R_5$ are defined as previously described, characterized in that (a) a compound having the following general formula (II):

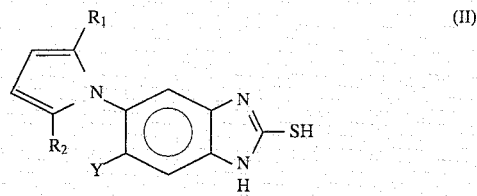

wherein Y, $R_1$ and $R_2$ are defined as previously described, is reacted with a compound having the following general formula (III):

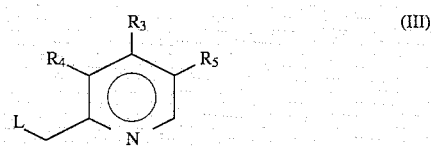

wherein $R_3$, $R_4$ and $R_5$ are defined as previously described and L represents halogen, esterified hydroxy or acyloxy, in an organic solvent in the presence of a base, or (b) a compound having the following general formula (IV):

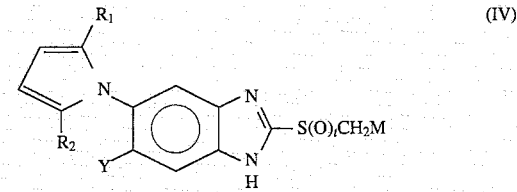

wherein Y, $R_1$ and $R_2$ are defined as previously described, t denotes 1 or 2 and M represents an alkali metal, is reacted with a compound having the following general formula (V):

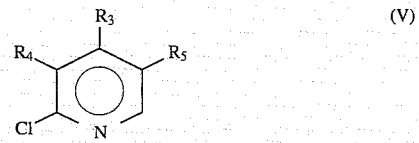

wherein $R_3$, $R_4$ and $R_5$ are defined as previously described, or (c) a compound having the following general formula (VI):

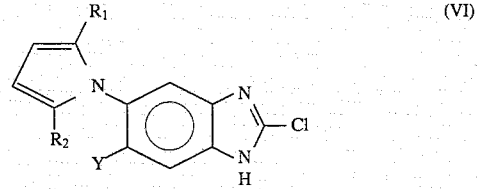

wherein Y, $R_1$ and $R_2$ are defined as previously described, is reacted with a compound having the following general formula (VII):

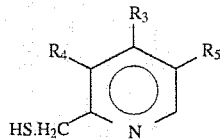

wherein $R_3$, $R_4$ and $R_5$ are defined as previously described, or (d) a compound having the following general formula (VIII):

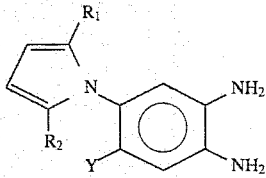

wherein Y, $R_1$ and $R_2$ are defined as previously described, is reacted with a compound having the following general formula (IX):

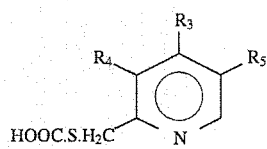

wherein $R_3$, $R_4$ and $R_5$ are defined as previously described, in a polar solvent in the presence of a strong acid.

The third object of the present invention is to provide an anti-ulcer composition containing a novel 5-pyrrolyl-6-halogeno-2-pyridylmethylsulfinylbenzimidazole derivative having the general formula (I), as defined above.

DISCLOSURE OF INVENTION

In one aspect, the present invention relates to a novel 5-pyrrolyl-6-halogeno-2-pyridylmethylsulfinylbenzimidazole derivative having the following general formula (I):

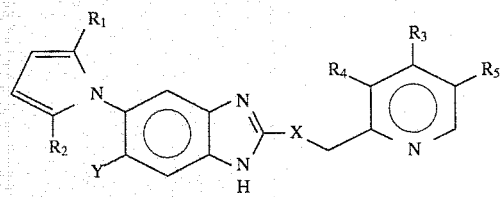

and a pharmaceutically acceptable salt thereof, in which

X represents S, SO or $SO_2$,

Y represents halogen, $R_1$ and $R_2$ independently from each other represent hydrogen or alkyl, $R_3$ represents hydrogen, $C_1$–$C_8$ alkyl, —$SR_6$, —$N(R_7)_2$, 1-piperidinyl, 4-morpholinyl, 4-methylpiperazin-1-yl, 1-pyrrolidinyl, or a group of formula —$OR_6$ or —$O(CH_2)_m$—Z, wherein $R_6$ represents $C_1$–$C_4$ alkyl, $C_2$–$C_4$ alkenyl, optionally substituted $C_3$–$C_{10}$ cycloalkyl, $C_2$–$C_5$ fluoroalkyl, or phenyl or benzyl, each of which is independently substituted with one or more halogen or $C_1$–$C_4$ alkyl or alkoxy optionally substituted with halogen, $R_7$ represents hydrogen or $C_1$–$C_5$ alkyl, Z represents a group of formula —$O(CH_2)_p$—$OR_8$, —$O(CH_2)_q$—$R_9$ or —$O(CH_2)_r O(CH_2)_s$—$OR_{10}$, wherein p and q independently from each other denote an integer of 1 to 3, r and s independently from each other denote an integer of 1 to 5, $R_8$ represents hydrogen, lower alkyl, aryl or aralkyl, $R_9$ represents hydrogen, alkoxycarbonyl, aryl or heteroaryl, and $R_{10}$ represents hydrogen or lower alkyl, m represents an integer of 2 to 10, and $R_4$ and $R_5$ independently from each other represent hydrogen or $C_1$–$C_5$ alkyl, or when $R_4$ and $R_5$ together with the carbon atoms adjacent to pyridine ring form a ring, $R_4$ and $R_3$ or $R_3$ and $R_5$ represent —CH=CH—CH=CH—, —$O(CH_2)_n$—, —$O(CH_2)_nO$—, —$CH_2(CH_2)_n$— or —OCH=CH—, wherein n denotes an integer of 1 to 4.

The preferred compounds of formula (I) according to the present invention include those wherein X represents S, SO or $SO_2$, Y represents halogen, $R_1$ and $R_2$ independently from each other represent hydrogen or methyl, $R_3$ represents hydrogen, $C_1$–$C_8$ alkyl, —$SR_6$, —$N(R_7)_2$, 1-piperidinyl, 4-morpholinyl, 4-methylpiperazin-1-yl, 1-pyrrolidinyl, or a group of formula —$OR_6$ or —$O(CH_2)_m$—Z, wherein $R_6$ represents $C_1$–$C_4$ alkyl, $C_2$–$C_4$ alkenyl, $C_3$–$C_{10}$ cycloalkyl optionally substituted with $C_1$–$C_4$ alkyl, $C_2$–$C_5$ fluoroalkyl having 3 to 8 fluorine atoms, or phenyl which is substituted with one or more halogen or $C_1$–$C_4$ alkyl or alkoxy optionally substituted with halogen, $R_7$ represents hydrogen or $C_1$–$C_4$ alkyl, Z represents a group of formula —$O(CH_2)_p$—$OR_8$, —$O(CH_2)_q$—$R_9$ or —$O(CH_2)_r O(CH_2)_s$—$OR_{10}$, wherein p and q independently from each other denote an integer of 1 to 3, r and s independently from each other denote an integer of 1 to 5, $R_8$ represents hydrogen, lower alkyl, aryl or aralkyl, $R_9$ represents hydrogen, alkoxycarbonyl, aryl or heteroaryl, and $R_{10}$ represents hydrogen or lower alkyl, m represents an integer of 2 to 10, and $R_4$ and $R_5$ independently from each other represent hydrogen or $C_1$–$C_5$ alkyl, or when $R_4$ and $R_5$ together with the carbon atoms adjacent to pyridine ring form a ring, $R_4$ and $R_3$ or $R_3$ and $R_5$ represent —CH=CH—CH=CH—, —$O(CH_2)_n$—, —$CH_2(CH_2)_n$— or —OCH=CH—, wherein n denotes an integer of 1 to 4 and the oxygen atom must be present in the $R_3$ position.

In the preferred definition of $R_6$ above, $C_2$–$C_4$ alkenyl includes, for example, 1-propenyl, 3-butenyl or their isomers; and the example of $C_3$–$C_{10}$ cycloalkyl may include unsubstituted or substituted cycloalkyl, for example, cyclopropyl, 2-methylcyclopropyl, 2,2-dimethylcyclopropyl, 2,3-diethylcyclopropyl, 2-butyl-cyclopropyl, cyclobutyl, 2-methylcyclobutyl, 3-propylcyclobutyl, 2, 3, 4-triethylcyclobutyl, 2,2-dimethylcyclohexyl, cycloheptyl, cyclooctyl, cyclononyl, cyclodecyl, etc. In addition, the example of "phenyl which is substituted with one or more halogen or $C_1$–$C_4$ alkyl or alkoxy optionally substituted with halogen" may include phenyl(o-, m- or p-)tolyl, (o-, m- or p-)ethylphenyl, 2-ethyltolyl, 4-ethyl-o-tolyl, 5-ethyl-m-tolyl, (o-, m- or p-)proethyltolyl, pylphenyl, 2-propyl-(o-, m- or p-)tolyl, 4-isopropyl-2,6-xylyl, 3-propyl-4-ethylphenyl, (2,3,4-, 2,3,6- or 2,4,5-) trimethylphenyl, (o-, m- or p-)fluorophenyl, (4-, 2,5-, 2,6-, 3,4- or 3,5-) difluorophenyl, (o-, m- or p-)chlorophenyl, 2-chloro-p-tolyl, (3-, 4-, 5- or 6-)chloro-o-tolyl, (o-, m- or p-trifluoromethyl)phenyl, 4-fluoro-2,5- xylyl, 4-chloro-2-propylphenyl, 2-isopropyl-4-chlorophenyl, 4-chloro-3,5-xylyl, (2,3-, 2,4-, 2,5-, 2,6- or 3,5)-dichlorophenyl, 4-chloro-3-fluorophenyl, (3- or 4-) chloro-2-fluorophenyl, (o-, m- or p-)trifluoromethylphenyl, (o-, m- or p-)ethoxyphenyl, (4- or p-(4- or 5-)chloro-2-methoxyphenyl or 2,4-dichloro-(5- or 6-)methylphenyl. The example of "$C_2$–$C_5$ fluoroalkyl" may include 2,2,2-trifluoroethyl, 2,2,3,3,3-pentafluoropropyl, 2,2,3,3-tetrafluoropropyl, 1-(trifluoromethyl)-2,2,2-trifluoroethyl, 2,2,3,3,4,4,4-heptafluorobutyl, 2,2,3,3,4,4,5,5-oxtafluoropentyl, and the like. In the definition of substituent Y, the term "halogen" means fluoro, chloro, bromo, etc.

The particularly preferred compounds of formula (I) according to the present invention include those wherein
X represents S, SO or $SO_2$,
Y represents fluoro,
$R_1$ and $R_2$ independently from each other represent hydrogen or methyl,
$R_3$ represents hydrogen, methyl, methoxy, ethoxy, ethoxyethoxy, 2,2,2-trifluoroethoxy or 3,3,3,2,2-pentafluoropropoxy,
$R_4$ represents hydrogen or methyl, and
$R_5$ represents hydrogen, methyl or ethyl.

In addition, the very particularly preferred compounds of formula (I) according to the present invention include those wherein
X represents SO,
Y represents fluoro,
$R_1$ and $R_2$ independently from each other represent hydrogen or methyl,
$R_3$ represents methoxy or ethoxy, and
$R_4$ and $R_5$ independently from each other represent hydrogen, methyl or ethyl.

In another aspect, the present invention relates to a process for preparing the novel compound of formula (I) as defined above.

According to the present invention, the compound of formula (I) can be prepared by reacting a compound of formula (II) with a compound of formula (III) in an organic solvent in the presence of a base as shown in the following reaction scheme (A):

In the reaction according to the above reaction scheme (A) of the present invention, the solvent which can be suitably used may include a common organic solvent, for example, lower alkanol such as methanol, ethanol, etc., acetone, ether, tetrahydrofuran, methylene chloride, acetonitrile, dimethylsulfoxide or dimethyl-formamide, to which water may optionally be added. The reaction temperature is generally in the range of approximately 0° C. to 150° C., preferably in the range of approximately 50° C. to 100° C.

As the base for this reaction, hydroxides, carbonates or hydrides of alkali metal or alkaline earth metal, or tertiary amines can be used, of which an example includes sodium hydroxide, potassium hydroxide, potassium carbonate, calcium carbonate, sodium methoxide, sodium hydrogen carbonate, potassium hydride, sodium hydride, pyridine, triethylamine, ethyldiisopropylamine, and the like.

The compound of formula (I) according to the present invention can be prepared by oxidizing the compound of formula (Ia) with a suitable amount of an oxidizing agent, as shown in the above reaction scheme (A). In this case, the resulting compound of formula (I) can be either a sulfoxide (—SO—) compound or a sulfone (—$SO_2$—) compound depending on the kind and amount of used oxidizing agent.

The oxidizing agent which can be used for this purpose include: m-chloroperoxybenzoic acid, hydrogen peroxide, peroxyacetic acid, trifluoroperoxyacetic acid, 3,5-dinitroperoxybenzoic acid, peroxymaleic acid, vanadium pentaoxide, nitric acid, ozone, dinitrogen tetraoxide, iodoxobenzene, N-halosuccinimide, 1-chlorobenzotriazole, t-butylhypochlorite, diazabicyclo [2,2,2]-octane, sodium metaperiodate, selenium dioxide, manganese dioxide, chromic acid, ceric ammonium nitrate, bromine, chlorine, sulfuryl chloride, and the like.

Preferably, this reaction can be carried out in an inert solvent, for example, an aromatic hydrocarbon such as benzene or toluene; a chlorinated hydrocarbon such as chloroform or methylene chloride; acetone, and the like.

In this case, the reaction temperature is generally in the range of –70° C. to the boiling point of the solvent used therein, preferably in the range of –50° C. to –20° C.

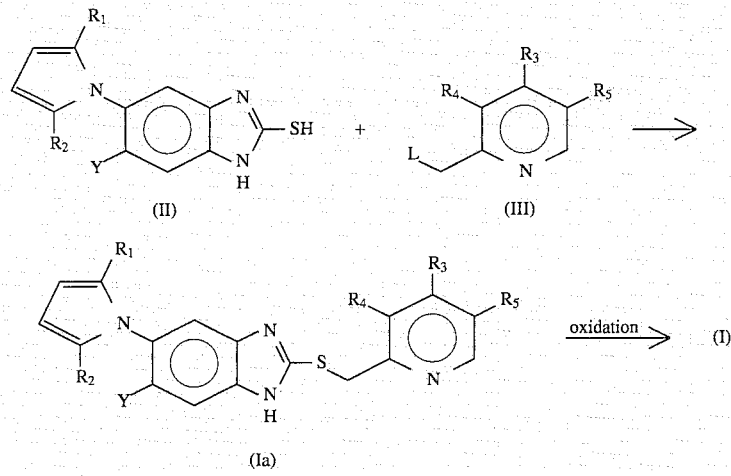

In the above reaction scheme,
Y, $R_1$, $R_2$, $R_3$, $R_4$ and $R_5$ are defined as in the compound of formula (I) above, and
L represents halogen, esterified hydroxy or acyloxy.

The compound of formula (I) according to the present invention can also be prepared by reacting a compound of formula (IV) with a compound of formula (V) as shown in the following reaction scheme (B):

In addition, the compound of formula (I) according to the present invention can also be prepared by reacting a compound of formula (VI) with a compound of formula (VII) as shown in the following reaction scheme (C):

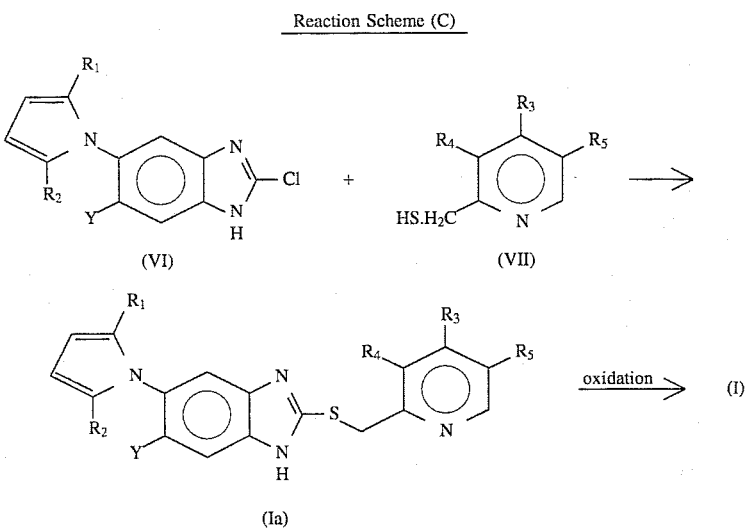

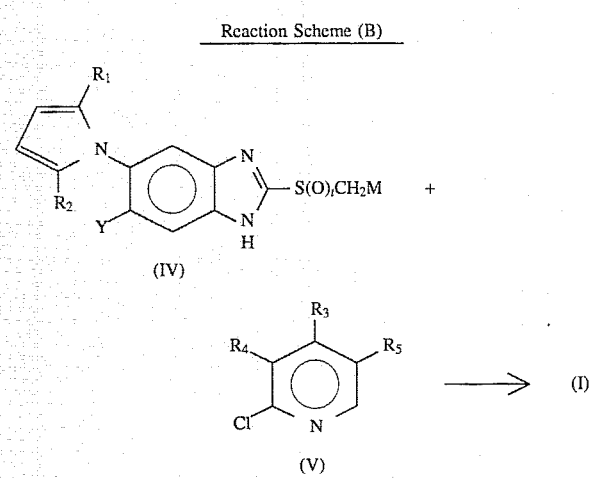

In the above reaction scheme Y, $R_1$, $R_2$, $R_3$, $R_4$ and $R_5$ are defined as in the compound of formula (I) above.

The reaction according to the above reaction scheme (C) can be conducted under the conditions which are substantially identical to those in the reaction according to the reaction scheme (A) for preparing the compound of formula (I) of the present invention.

In addition, the compound of formula (Ia) produced according to the above method can be oxidized under the same conditions as in the reaction scheme (A) above, to prepare the sulfone or sulfoxide compound of formula (I) according to the present invention.

Alternatively, the compound of formula (I) according to the present invention can be prepared by reacting a compound of formula (VIII) with a compound of formula (IX) in a polar solvent in the presence of a strong acid, as shown in the following reaction scheme (D):

In the above reaction scheme,
Y, $R_1$, $R_2$, $R_3$, $R_4$ and $R_5$ are defined as in the compound of formula (I) above,
t denotes 1 or 2, and
M represents an alkali metal.

The reaction according to the reaction scheme (B) can preferably be carried out in a conventional inert solvent. For this purpose, the solvent which can be suitably used includes the organic solvent as mentioned in connection with the reaction scheme (A) above. In addition, the reaction is carried out generally at the temperature of 0° C. to 120° C., preferably at the boiling point of the solvent used therein.

The compound of formula (V) which is used as the starting material in the method according to the reaction scheme (B) for preparing the compound of formula (I) of the present invention can be prepared by reacting a pyridine N-oxide intermediate with a conventional chlorinating agent such as phosphorus oxychloride, phosphorus pentachloride, and the like.

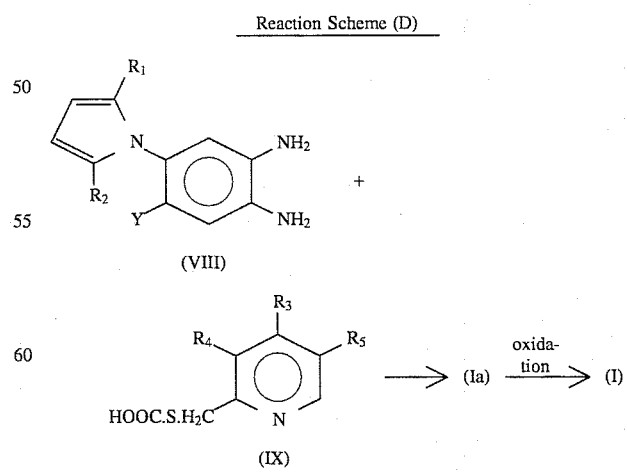

In the above reaction scheme Y, $R_1$, $R_2$, $R_3$, $R_4$ and $R_5$ are defined as in the compound of formula (I) above.

In the reaction according to the above reaction scheme (D), the polar solvent may also contain water. This reaction can be preferably carried out at the boiling point of the solvent used therein.

The compound of formula (Ia) which is produced according to the reaction scheme (C) or (D) can be oxidized according to the same procedure as in the reaction scheme (A) to prepare the sulfone or sulfoxide compound of formula (I) of the present invention.

The starting materials used in the above mentioned processes according to the present invention are presently known and can be prepared according to known methods.

The compound of formula (I) prepared by the above mentioned processes according to the present invention can be separated and purified according to conventional working up procedures or can be converted into a pharmaceutically acceptable salt form thereof according to conventional methods.

The compound of formula (I) according to the present invention can be used for prophylaxis and treatment of gastric and duodenal ulcers. The compound of formula (I) has a chemical structure similar to that of the known anti-ulcer agent, Omeprazole, and therefore exhibits a similar pharmacological acting mechanism to that of Omeprazole. Further, as demonstrated from both in vitro and in vivo tests, the pharmacological efficacy of the compound of formula (I) according to the present invention is stronger than that of Omeprazole. In addition, according to the pharmacological toxicity test it has been identified that the compound of formula (I) according to the present invention has substantially no acute toxicity or CNS and cardiovascular toxicities.

Accordingly, the novel compound of formula (I) according to the present invention is an excellent anti-ulcer agent which has a superior pharmacological effect far better than that of any known anti-ulcer agent and also a prolonged duration of action.

The compound of formula (I) according to the present invention can be administered either per orally or parenterally. The preferred route of administration is per oral.

The compound of formula (I) according to the present invention can be administered itself or in the form of a pharmaceutically acceptable salt thereof. Suitable examples of such salts of the compound of formula (I) include an acid addition salt and an alkali metal salt. As the alkali metal salt, sodium salt, potassium salt, lithium salt, magnesium salt, calcium salt or alkylamino salt can be mentioned. As an acid which can form the acid addition salt of the compound of formula (I), the following can be mentioned: sulfonic acid, phosphoric acid, nitric acid, perchloric acid, formic acid, acetic acid, propionic acid, succinic acid, gluconic acid, lactic acid, malic acid, tartaric acid, citric acid, ascorbic acid, maleic acid, hydroxymaleic acid, pyruvic acid, phenylacetic acid, benzoic acid, p-aminobenzoic acid, p-hydroxybenzoic acid, salicylic acid, p-aminosalicylic acid, ambonic acid, methanesulfonic acid, ethane-sulfonic acid, hydroxyethanesulfonic acid, ethylenesulfonic acid, toluenesulfonic acid, naphthylsulfonic acid, sulfanilic acid, camphorsulfonic acid, quinic acid, o-methylenemandelic acid, hydrogenbenzene sulfonic acid, methionine, tryptophane, lysine, arginine, picric acid, d-o-tolyl-tartaric acid, and the like.

The compound of formula (I) according to the present invention can be administered in a suitable pharmaceutically acceptable formulation which is prepared by using a pharmaceutically acceptable additive and a suitable carrier by methods well known to those skilled in the related art. Although such formulation includes various pharmaceutically acceptable formulations such as capsules, tablets, suppositories, sustained release formulations, sugar-coated tablets, syrups or injections, the capsule or tablet formulations are preferably administered.

The compound of this invention can be employed in admixture with conventional excipients, i.e. pharmaceutically acceptable organic or inorganic carrier substances suitable for parenteral, enteral (e.g. oral) administration which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, and the like. The pharmaceutical preparations can be sterilized and, if desired, mixed with auxiliary agents, e.g. preservatives, stabilizers, emulsifiers, salts for influencing osmotic pressure, buffers, coloring, flavoring and/or aromatic substances, and the like which do not deleteriously react with the active compounds. They can also be combined with other active agents, e.g. vitamins.

When the compound of formula (I) according to the present invention is administered to adult human patients for the prophylaxis and treatment of gastric and duodenal ulcers, the daily dosage of the compound of formula (I) can be varied depending on various factors including severity of ulcers, sex, age and conditions of patients, and the like, but is generally in the range of 0.05 to 10 mg, preferably 0.1 to 1.5 mg, per kg of body weight. The daily dosage of the compound of formula (I) can be administered at one time or over several times.

The present invention will be more specifically illustrated by the following examples. However, it should be understood that the present invention will not be limited to these examples.

PREPARATION EXAMPLE

EXAMPLE 1

Preparation of 2-[[(4-methoxy-3-methyl)-2-pyridinyl]methylthio]-5-(1H-pyrrol-1-yl)-6-fluoro-1H-benzimidazole (Compound 1)

5 g (21.43 mmole) of 5 (1H-pyrrol-1-yl) -6-fluoro-2-mercaptobenzimidazole and 1.89 g (2 eq. wt.) of sodium hydroxide were successively dissolved in 200 ml of methanol. To the resulting solution was added 4.46 g (1 eq. wt.) of 4-methoxy-3-methyl-2-chloromethylpyridine hydrochloride and then the mixture was stirred for 3 hours at 50° to 60° C. After the reaction is completed, the reaction mixture was filtered to remove the precipitated inorganic material. The filtrate was distilled under reduced pressure to remove the solvent and then the residue was crystallized from ethyl acetate, hexane and ether to obtain 7.14 g (Yield: 86.8%) of the title compound.

Melting Point: 150° C.

$^1$H-NMR $\delta$[DMSO-$d_6$]: 2.2(s, 3H), 3.9(s, 3H), 4.7(s, 2H), 6.3(t, 2H), 7.0(d, 1H), 7.1(t, 2H), 7.5(bs, 2H), 8.3(d, 1H)

EXAMPLE 2

Preparation of 2-[[(4-methoxy-3-methyl)-2-pyridinyl]methylsulfinyl]-5-(1H-pyrrol-1-yl)-6-fluoro-1H-benzimidazole (Compound 2)

6 g (16.29 mmole) of the compound prepared in EXAMPLE 1 was dissolved in 200 ml of acetone and then cooled down to −40° C. The solution of 4.69 g of m-chloroperoxybenzoic acid (50–60%) dissolved in 30 ml of acetone was slowly added dropwise thereto and then the mixture was stirred for 30 minutes while maintaining the temperature of −40° C. After the reaction is completed, to the reaction mixture was added hexane to crystallize the product which is then filtered and washed several times with ether to obtain 5.92 g (Yield: 94.6%) of the title compound.

Melting Point: 170° C.

$^1$H-NMR δ[DMSO-$d_6$]: 2.1 (s, 3H), 3.9(s, 3H), 4.7–4.8(dd, 2H), 6.3(t, 2H), 7.0(d, 1H), 7.1(t, 2H), 7.7(m, 2H), 8.2(d, 1H)

Compounds 3, 4, 5, 7, 8 and 9 listed in the following Tables 1 and 2 were prepared according to the same procedure as EXAMPLE 2.

EXAMPLE 3

Preparation of 2-[[(4-(2-ethoxyethoxy)-3-methyl)-2-pyridinyl]methylsulfinyl]-5-(1H-pyrrol-1-yl)-6-fluoro-1H-benzimidazole (Compound 6)

3 g (12.86 mmole) of 5-(1H-pyrrol-1-yl)-6-fluoro-2-mercapto-benzimidazole and 1.13 g (2 eq. wt.) of sodium hydroxide were successively dissolved in 150 ml of methanol. To the resulting solution was added 3.42 g (1 eq. wt.) of 4-(2-ethoxyethoxy)-3-methyl-2-chloromethylpyridine hydrochloride and then the mixture was allowed to react for 3 hours at 50° to 60° C. After removing the solvent under reduced pressure, the resulting product was dissolved in 150 ml of chloroform and then cooled down to −40° C. To this reaction solution was slowly added dropwise m-chloroperoxybenzoic acid (1 eq. wt.) and then the mixture was stirred for 30 minutes while maintaining the temperature of −40° C. Then, the solvent was removed from the reaction mixture under reduced pressure and the residue was purified by column chromatography (ethyl acetate:hexane=3:1) to obtain 2.94 g (Yield: 51.8%) of the title compound.

Melting Point: 84° C.

$^1$H-NMR δ[DMSO-$d_6$]: 1.1(t, 3H), 2.2(s, 3H), 3.6(q, 2H), 3.8(t, 2H), 4.2(t, 2H), 4.7–4.9(dd, 2H), 6.3(t, 2H), 7.0(d, 1H), 7.2(t, 2H), 7.7(m, 2H), 8.2(d, 1H)

EXAMPLE 4

Preparation of 2-[[(4-(2,2,2-trifluoroethoxy)-3,5-dimethyl)-2-pyridinyl] methylsulfinyl]-5- (1H-pyrrol-1-yl) -6-fluoro-1H-benzimidazole (Compound 10)

3 g (12.86 mmole) of 5-(1H-pyrrol-1-yl)-6-fluoro-2-mercaptobenzimidazole and 1.13 g (2 eq. wt.) of sodium hydroxide were successively dissolved in 150 ml of methanol. To the resulting solution was added 3.73 g (1 eq. wt.) of 4-(2,2,2-trifluoroethoxy)-3,5-dimethyl-2-chloromethylpyridine hydrochloride and then the mixture was allowed to react for 3 hours at 50° to 60° C. After removing the solvent under reduced pressure, the resulting product was dissolved in 150 ml of chloroform and then cooled down to −40° C. To this reaction solution was slowly added dropwise m-chloroperoxybenzoic acid (1 eq. wt.) and then the mixture was stirred for 30 minutes while maintaining the temperature of −40° C., washed with sodium bicarbonate and saturated saline, and dried with sodium sulfate. After removing the solvent under reduced pressure, the residue was crystallized from ethyl acetate, ether and hexane to obtain 4.38g (Yield : 76.0%) of the title compound.

Melting Point: 190°–192° C.

$^1$H-NMR δ[DMSO-$d_6$]: 2.2(s, 6H), 4.6(q, 2H), 4.7–4.9(dd, 2H), 6.2(t, 2H), 7.1(t, 2H), 7.6(m, 2H), 8.2(s, 1H)

Compounds 11 to 14 listed in the following Tables 1 and 2 were prepared. according to the same procedure as EXAMPLE 4.

EXAMPLE 5

Preparation of 2-[[(4-methoxy-3-methyl)-2-pyridinyl]methylsulfinyl]-5-(1H-2,5-dimethylpyrrol-1-yl)-6-fluoro-1H-benzimidazole (Compound 16).

4g (15.31 mmole) of 5-(1H-2,5-dimethylpyrrol-1-yl)-6-fluoro-2-mercaptobenzimidazole and 1.35 g (2 eq. wt.) of sodium hydroxide were successively dissolved in 200 ml of methanol. To the resulting solution was added 3.18 g (1 eq. wt.) of 4-methoxy-3-methyl-2-chloromethylpyridine hydrochloride and then the mixture was allowed to react for 3 hours at 50° to 60° C. After removing the solvent under reduced pressure, the resulting product was dissolved in 200 ml of chloroform and then cooled down to −40° C. To this reaction solution was slowly added dropwise m-chloroperoxybenzoic acid (1 eq. wt.) and then the mixture was stirred for 30 minutes while maintaining the temperature of −40° C. After removing the solvent from the reaction mixture at 40° C. under reduced pressure, the residue was subjected to column chromatography (ethyl acetate:hexane=3:1) to obtain 4.23g (Yield: 67.1%) of the title compound.

Melting Point: 112° C.

$^1$H-NMR δ[DMSO-$d_6$]: 1.9(s, 6H), 2.1(s, 3H), 3.8(s, 3H), 4.6–4.8 (dd, 2H), 5.8(s, 2H), 7.0(d, 1H), 7.6(m, 2H), 8.1(d, 1H)

Compounds 15 to 23 listed in the following Tables 1 and 2 were prepared according to the same procedure as EXAMPLE 5.

EXAMPLE 6

Preparation of 2-[[(4-methoxy-3-methyl)-2-pyridinyl]methylsulfinyl]-5-(1H-pyrrol-1-yl)-6-fluoro-1H-benzimidazole sodium salt (Compound 24)

1.3 g (3.38 mmole) of the compound prepared in EXAMPLE 2 was dissolved in 20 ml of methylene chloride and then 1.35 g (1 eq. wt.) of sodium hydroxide dissolved in 10 ml of water was added thereto. The mixture was then stirred for 20 minutes. The aqueous layer was separated, washed several times with methylene chloride and then lyophilized to obtain 1.12 g (Yield : 81.8%) of the title compound.

Melting Point: 232°–234° C.

$^1$H-NMR δ[$D_2O$]: 1.9(s, 3H), 3.8(s, 3H), 4.5–4.8(dd, 2H), 6.4(t, 2H), 6.9(d, 1H), 7.1(t, 2H), 7.4(d, 1H), 7.6(d, 1H), 8.2(d, 1H)

The sodium salts of other compounds of formula (I) can be prepared according to the same procedure as EXAMPLE 6.

EXAMPLE 7

Preparation of 2-[[(4-methoxy-3-methyl)-2-pyridinyl]methylsulfinyl]-5-(1H-pyrrol-1-yl)-6-fluoro-1H-benzimidazole (Compound 2)

5 g (18.59 mmole) of 2-(lithiummethylsulfinyl)-5-(1H-pyrrol-1-yl)-6-fluoro-benzimidazole was dissolved in 200 ml of benzene and then 2.93 g (1 eq. wt.) of 2-chloro-(4-methoxy-3-methyl)-pyridine was added thereto. The reaction mixture was refluxed for 2 hours and filtered to remove lithium chloride. After removing the solvent from the reaction mixture under reduced pressure, the resulting crude product was dissolved in ethyl acetate and then crystallized from ether to obtain 5.82 g (Yield : 81.5%) of the title compound.

Melting Point: 170° C.

$^1$H-NMR δ[DMSO-d$_6$]: 2.1(s, 3H), 3.9(s, 3H), 4.7–4.8(dd, 2H), 6.3(t, 2H), 7.0(d, 1H), 7.1(t, 2H), 7.7(m, 2H), 8.2(d, 1H)

EXAMPLE 8

Preparation of 2-[[(4-methoxy-3-methyl)-2-pyridinyl]methylthio]-5-(1H-pyrrol-1-yl)-6-fluoro-1H-benzimidazole (Compound 1)

6 g (35.50 mmole) of 4-methoxy-3-methyl-2-thiomethylpyridine was dissolved in a solution of 1.56 g (1.1 eq. wt.) of sodium hydroxide in 250 ml of methanol. To the resulting solution was added 8.36 g (1 eq. wt.) of 2-chloro-5-(1H-pyrrol-1-yl)-6-fluorobenzimidazole and then the reaction mixture was refluxed for 2 hours. After removing the solvent from the reaction mixture under reduced pressure, the resulting product was crystallized from ether to obtain 10.85 g (Yield : 83.0%) of the title compound.

Melting Point: 150° C.

$^1$H-NMR δ[DMSO-d$_6$]: 2.2(s, 3H), 3.9(s, 3H), 4.7(s, 2H), 6.3(t, 2H), 7.0(d, 1H), 7.1(t, 2H), 7.5(bs, 2H), 8.3 (d, 1H)

EXAMPLE 9

Preparation of 2-[[(4-methoxy-3-methyl),2-pyridinyl]methylthio]-5-(1H-pyrrol-1-yl)-6-fluoro-1H-benzimidazole (Compound 1)

5.58 g (26.18 mmole) of 2-[ [2-(4-methoxy-3-methyl)pyridinyl]methylthio]formic acid and 5 g (1 eq. wt.) of 5-(1H-pyrrol-1-yl)-6-fluoro-2,3-diaminobenzene were refluxed in 150 ml of 4N HCl for 40 minutes. The reaction mixture was cooled down and then neutralized with ammonia water. The reaction solution was treated with active carbon and extracted with ethyl acetate. The extract was distilled under reduced pressure to remove the solvent and then the residue was crystallized from ether to obtain 2.75 g (Yield: 28.6%) of the title compound.

Melting Point: 150° C.

$^1$H-NMR δ[DMSO-d$_6$]: 2.2(s, 3H), 3.9(s, 3H), 4.7(s, 2H), 6.3(t, 2H), 7.0(d, 1H), 7.1(t, 2H), 7.5(bs, 2H), 8.3 (d, 1H)

The physico-chemical properties of the respective compound of formula (I) prepared according to the substantially same procedure as the above EXAMPLES 1 to 9 are described in the following Tables 1 and 2.

TABLE 1

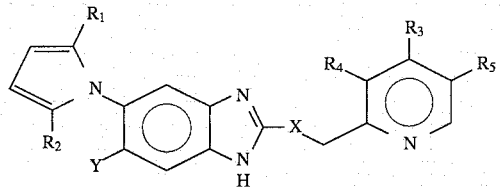

(I)

| Compound No. | X | Y | R$_1$ | R$_2$ | R$_3$ | R$_4$ | R$_5$ | m.p. (°C.) | Yield (%) |
|---|---|---|---|---|---|---|---|---|---|
| 1 | S | F | H | H | OCH$_3$ | CH$_3$ | H | 150 | 87 |
| 2 | SO | F | H | H | OCH$_3$ | CH$_3$ | H | 170 | 95 |
| 3 | SO | F | H | H | OCH$_3$ | H | CH$_3$ | 182 | 85 |
| 4 | SO | F | H | H | OCH$_3$ | CH$_3$ | CH$_3$ | 180 | 83 |
| 5 | SO | F | H | H | OCH$_2$CH$_3$ | CH$_3$ | H | 144 | 76 |
| 6 | SO | F | H | H | OCH$_2$CH$_2$OCH$_2$CH$_3$ | CH$_3$ | H | 84 | 52 |
| 7 | SO | F | H | H | OCH$_3$ | OCH$_3$ | H | 169 | 72 |
| 8 | SO | F | H | H | OCH$_3$ | H | H | 194 | 83 |
| 9 | SO | F | H | H | H | H | H | 188 | 80 |
| 10 | SO | F | H | H | OCH$_2$CF$_3$ | CH$_3$ | CH$_3$ | 190–192 | 76 |
| 11 | SO | F | H | H | OCH$_2$CF$_2$CF$_3$ | CH$_3$ | CH$_3$ | 184–186 | 82 |
| 12 | SO | F | H | H | OCH$_2$CF$_2$CF$_3$ | CH$_3$ | H | 98 | 85 |
| 13 | SO | F | H | H | OCH$_2$CF$_2$CF$_2$CF$_3$ | CH$_3$ | H | 148–150 | 78 |
| 14 | SO$_2$ | F | H | H | OCH$_2$CF$_2$CF$_3$ | CH$_3$ | H | 98–100 | 83 |
| 15 | SO | F | CH$_3$ | CH$_3$ | OCH$_3$ | CH$_3$ | CH$_3$ | 104 | 55 |
| 16 | SO | F | CH$_3$ | CH$_3$ | OCH$_3$ | CH$_3$ | H | 112 | 67 |
| 17 | SO | F | CH$_3$ | CH$_3$ | OCH$_3$ | H | CH$_3$ | 220–224 | 60 |
| 18 | SO | F | CH$_3$ | CH$_3$ | CH$_3$ | H | CH$_3$ | 98–100 | 62 |
| 19 | SO | F | CH$_3$ | CH$_3$ | OCH$_3$ | OCH$_3$ | H | 96–98 | 50 |
| 20 | SO | F | CH$_3$ | CH$_3$ | OCH$_3$ | H | H | 120–122 | 68 |
| 21 | SO | F | CH$_3$ | CH$_3$ | H | H | H | 84–86 | 62 |
| 22 | SO | F | CH$_3$ | CH$_3$ | OCH$_2$CF$_3$ | CH$_3$ | CH$_3$ | 92–94 | 59 |
| 23 | SO | F | CH$_3$ | CH$_3$ | OCH$_2$CF$_3$ | CH$_3$ | H | 97–98 | 50 |
| 24 | | | | | Sodium salt of Compound 2 | | | 232–234 | 82 |
| 25 | | | | | Sodium salt of Compound 16 | | | 240 | 80 |

TABLE 2

| Compound No. | $^1$H-NMR δ(DMSO-d$_6$) |
|---|---|
| 1 | 2.2(s, 3H), 3.9(s, 3H), 4.7(s, 2H), 6.3(t, 2H), 7.0(d, 1H), 7.1(t, 2H), 7,5(bs, 2H), 8.3(d, 1H) |
| 2 | 2.1(s, 3H), 3.9(s, 3H), 4.7–4.8(dd, 2H), 6.3(t, 2H), 7.0(d, 1H), 7.1(t, 2H), 7,7(m, 2H), 8.2(d, 1H) |
| 3 | 2.1(s, 3H), 3.7(s, 3H), 4.5–4.7(dd, 2H), 6.3(t, 2H), 6.8(s, 1H), 7.1(t, 2H), 7.7(m, 2H), 8.1(s, 1H) |
| 4 | 2.2(s, 6H), 3.7(s, 3H), 4.7–4.9(dd, 2H), 6.3(t, 2H), 7.2(t, 2H), 7.7(m, 2H), 8.2(s, 1H) |
| 5 | 1.4(t, 3H), 2.1(s, 3H), 4.1(q, 2H), 4.6–4.8(dd, 2H), 6.3(t, 2H), 7.0(d, 1H), 7.2(t, 2H), 7.7(m, 2H), 8.2(d, 1H) |
| 6 | 1.1(t, 3H), 2.2(s, 3H), 3.6(q, 2H), 3.8(t, 2H), 4.2(t, 2H), 4.7–4.9(dd, 2H), 6.3(t, 2H), 7.0(d, 1H), 7.2(t, 2H), 7.7(m, 2H), 8.2(d, 1H) |
| 7 | 3.8(s, 3H), 3.9(s, 3H), 4.6–4.8(dd, 2H), 6.3(t, 2H), 7.1(m, 2H), 7.7(bs, 2H), 8.1(s, 1H) |
| 8 | 3.8(s, 3H), 4.5–4.8(dd, 2H), 6.3(t, 2H), 6.7(s, 2H), 7.2(t, 2H), 7.7(m, 2H), 8.4(d, 1H) |
| 9 | 4.7–4.9(dd, 2H), 6.3(t, 2H), 7.2(t, 2H), 7.4(m, 2H), 7.8(m, 3H), 8.6(d, 1H) |
| 10 | 2.2(s, 6H), 4.6(q, 2H), 4.7–4.9(dd, 2H), 6.2(t, 2H), 7.1(t, 2H), 7.6(m, 2H), 8.2(s, 1H) |
| 11 | 2.2(s, 6H), 4.6(t, 2H), 4.7–4.9(dd, 2H), 6.2(t, 2H), 7.1(t, 2H), 7.6(m, 2H), 8.2(s, 1H) |
| 12 | 2.2(s, 3H), 4.7–4.8(dd, 2H), 5.0(t, 2H), 6.3(t, 2H), 7.1(t, 2H), 7.6–7.8(m, 2H), 8.3(d, 1H) |
| 13 | 2.1(s, 3H), 4.7–4.9(dd, 2H), 5.0(t, 2H), 6.3(t, 2H), 7.2(t, 2H), 7.4(d, 1H), 7.6–7.8(m, 2H), 8.3(d, 1H) |
| 14 | 2.2(s, 3H), 4.8(t, 2H), 4.9–5.1(dd, 2H), 6.3(t, 2H), 7.1(d, 1H), 7.2(t, 2H), 7.6–7.8(m, 2H), 8.3(d, 1H) |
| 15 | 1.9(s, 6H), 2.2(s, 6H), 3.7(s, 3H), 4.7–4.9(dd, 2H), 5.8(s, 2H), 7.7(m, 2H), 8.2(s, 1H) |
| 16 | 1.9(s, 6H), 2.1(s, 3H), 3.8(s, 3H), 4.6–4.8(dd, 2H), 5.8(s, 2H), 7.0(d, 1H), 7.6(m, 2H), 8.1(d, 1H) |
| 17 | 1.9(s, 6H), 2.1(s, 3H), 3.8(s, 3H), 4.5–4.8(dd, 2H), 5.8(s, 2H), 7.1(s, 1H), 7.5–7.8(m, 2H), 8.3(s, 1H) |
| 18 | 2.0(s, 6H), 2.2(s, 6H), 4.5–4.8(dd, 2H), 5.9(s, 2H), 7.1(s, 1H), 7.5–7.8(m, 2H), 8.3(s, 1H) |
| 19 | 1.9(s, 6H), 3.8(s, 3H), 3.9(s, 3H), 4.6–4.8(dd, 2H), 5.8(s, 2H), 7.1(d, 1H), 7.5–7.7(m, 2H), 8.2(d, 1H) |
| 20 | 1.9(s, 6H), 3.7(s, 3H), 4.6–4.8(dd, 2H), 5.9(s, 2H), 6.9(s, 1H), 7.0(d, 1H), 7.6–7.8(m, 2H), 8.3(d, 1H) |
| 21 | 1.9(s, 6H), 4.6–4.8(dd, 2H), 5.8(s, 2H), 7.3–7.9 (m, 5H), 8.5(d, 1H) |
| 22 | 1.9(s, 6H), 2.2(s, 3H), 4.6(q, 2H), 4.7–4.9(dd, 2H), 5.8(s, 2H), 7.6(m, 2H), 8.2(s, 1H) |
| 23 | 1.9(s, 6H), 2.2(s, 3H), 4.7–4.9(dd, 2H), 5.0(q, 2H), 5.9(s, 2H), 7.1(d, 1H), 7.5–7.7(m, 2H) |
| | $^1$H-NMR δ (D$_2$O) |
| 24 | 1.9(s, 3H), 3.8(s, 3H), 4.5–4.8(dd, 2H), 6.4(t, 2H), 6.9(d, 1H), 7.1(t, 2H), 7.4(d, 1H), 7.6(d, 1H), 8.2(d, 1H) |
| 25 | 1.9–2.0(bs, 9H), 3.8(s, 3H), 4.4–4.9(dd, 2H), 6.0 (s, 2H), 6.85(d, 1H), 7.5(m, 2H), 8.2(d, 1H) |

Anti-ulcer effect of the compound of formula (I), as defined above, according to the present invention has been demonstrated by various experiments including the inhibition of enzyme activity, the effect of inhibition of gastric juice secretion and acidity, ED$_{50}$ and the like. The test methods and results are as follows.

PHARMACOLOGICAL TEST

TEST 1: Inhibition of enzyme activity

The inhibition of H$^+$/K$^+$-ATPase by the compound of formula (I) according to the present invention was demonstrated by in vitro testing.

In this test, Omeprazole [5-methoxy-2-[[(4-methoxy-3,5-dimethyl-2-pyridinyl)methyl]sulfinyl]-1H-benzimidazole] was used as the control compound.

The gastric mucous membrane was removed from rabbit and then centrifuged with 77,000 xg using a ultracentrifuge to separate the microsomal fraction which was used as the source of H$^+$/K$^+$-ATPase enzyme for this test. 60 μg of H$^+$/K$^+$-ATPase was pre-incubated with the sample (the compound according to the present invention) for 5 minutes at 37° C. and then 4 mM ATP as the substrate and 4 mM Mg$^{++}$, 20 mM K$^+$ as the cofactor were added thereto. Then, the amount of inorganic phosphorus thus produced was determined using a spectrophotometer at 660 nm and converted into the amount of protein according to Lowry method. The concentration of the compound which inhibits the enzyme activity by 50%, i.e. IC$_{50}$ was calculated from the percentage values for enzyme activity ihibition which were obtained from 3 to 5 test tubes containing different concentration of the sample compound, according to Litchfield-Wilcoxon method. The results thereof are described in the following Table 3.

TABLE 3

| Compound No. | IC$_{50}$ (M) |
|---|---|
| 1 | $4.2 \times 10^{-4}$ |
| 2 | $4.1 \times 10^{-6}$ |
| 3 | $2.0 \times 10^{-3}$ |
| 4 | $4.3 \times 10^{-4}$ |
| 5 | $<<4.0 \times 10^{-5}$ |
| 6 | $2.8 \times 10^{-5}$ |
| 7 | $2.9 \times 10^{-4}$ |
| 8 | $1.9 \times 10^{-3}$ |
| 9 | $4.7 \times 10^{-3}$ |
| 10 | — |
| 11 | $9.3 \times 10^{-3}$ |
| 12 | $1.5 \times 10^{-4}$ |
| 13 | $4.7 \times 10^{-4}$ |
| 14 | $5.3 \times 10^{-3}$ |
| 15 | $5.0 \times 10^{-5}$ |
| 16 | $1.2 \times 10^{-5}$ |
| 17 | $2.2 \times 10^{-5}$ |
| 18 | $4.0 \times 10^{-4}$ |
| 19 | $8.1 \times 10^{-3}$ |
| 20 | $2.1 \times 10^{-4}$ |
| 21 | $7.6 \times 10^{-3}$ |
| 22 | $3.9 \times 10^{-4}$ |
| 23 | $3.2 \times 10^{-4}$ |
| 24 | $5.6 \times 10^{-6}$ |
| 25 | $5.9 \times 10^{-6}$ |
| Omeprazole | ca. $1.6 \times 10^{-4}$ |

As the second in vivo test, the tests for the inhibition of gastric juice secretion and acidity were conducted with rats using the Shay method and the results were compared with the normal control group and the Omeprazole group. The specific test methods are as follows.

SD male rats (200±20 g) were fasted for 24 hours, except for water, and then anesthesized with ether. The abdomen of rats was incised and then the pylorus was ligated. The test compounds were suspended or dissolved in 0 to 5% CMC (carboxymethylcellulose) and injected into duodenum. After the abdomen was suctured, the rats were allowed to stand for 5 hours and then sacrificed with ether. The stomach was removed from rats and the gastric juices were collected. The gastric juice was centrifuged with 10,000xg for 10 minutes at 4° C. to remove the precipitate. The amount of gastric juice and acidity were determined using pH 7.0 end point assay with 0.02N NaOH and then the total acid output was calculated.

The results thereof are described in the following Tables 4 and 5.

TABLE 4

Effect on inhibition of gastric juice secretion

| | Dose (mg/kg) | Number of animals | Volume (ml/ 100 g BW) | Inhibition rate (%) |
|---|---|---|---|---|
| Normal Group | | 6 | 3.26 ± 0.31 | — |
| Omeprazole | 10 | 6 | 1.49 ± 0.18 | 54.29 |
| Compound 2 | 3 | 6 | 2.11 ± 0.36 | 35.28 |
| | 10 | 6 | 1.52 ± 0.19 | 53.37 |
| | 30 | 6 | 1.03 ± 0.10 | 68.40 |
| Normal Group | | 6 | 2.83 ± 0.19 | — |
| Compound 5 | 10 | 6 | 1.63 ± 0.04 | 42.40 |
| | 30 | 6 | 1.21 ± 0.10 | 57.24 |
| Normal Group | | 6 | 2.73 ± 0.21 | — |
| Compound 15 | 10 | 6 | 1.81 ± 0.19 | 33.70 |
| | 30 | 6 | 1.46 ± 0.13 | 46.52 |
| Normal Group | | 6 | 3.45 ± 0.23 | — |
| Compound 16 | 3 | 6 | 1.92 ± 0.14 | 44.35 |
| | 10 | 6 | 1.35 ± 0.15 | 60.87 |
| | 30 | 6 | 0.98 ± 0.19 | 71.59 |
| Normal Group | | 6 | 3.04 ± 0.24 | — |
| Compound 20 | 10 | 6 | 1.41 ± 0.16 | 53.62 |
| | 30 | 6 | 1.06 ± 0.10 | 65.13 |

TABLE 5

Effect on inhibition of acidity

| | Dose (mg/kg) | Number of animals | Volume (μEq/hr) | Inhibition rate (%) |
|---|---|---|---|---|
| Normal Group | | 6 | 57.93 ± 9.72 | — |
| Omeprazole | 10 | 6 | 9.91 ± 4.20 | 82.89 |
| Compound 2 | 3 | 6 | 34.60 ± 8.12 | 40.62 |
| | 10 | 6 | 14.28 ± 4.28 | 75.35 |
| | 30 | 6 | 5.72 ± 0.59 | 90.13 |
| Normal Group | | 6 | 65.78 ± 4.61 | — |
| Compound 5 | 10 | 6 | 21.85 ± 2.44 | 66.78 |
| | 30 | 6 | 11.84 ± 4.00 | 82.00 |
| Normal Group | | 6 | 55.22 ± 6.97 | — |
| Compound 15 | 10 | 6 | 26.61 ± 5.27 | 51.81 |
| | 30 | 6 | 12.74 ± 1.80 | 76.93 |
| Normal Group | | 6 | 72.63 ± 11.43 | — |
| Compound 16 | 3 | 6 | 25.65 ± 6.86 | 64.68 |
| | 10 | 6 | 10.08 ± 3.71 | 86.12 |
| | 30 | 6 | 1.75 ± 1.06 | 97.59 |
| Normal Group | | 6 | 71.44 ± 7.39 | — |
| Compound 20 | 10 | 6 | 18.41 ± 2.27 | 74.23 |
| | 30 | 6 | 11.31 ± 1.91 | 84.17 |

As can be seen from the above test results, among the compound of formula (I) according to the present invention Compounds 2, 5, 16 and 20 exhibit a similar or superior enzyme inhibition activity to the known anti-ulcer agent, Omeprazole. particularly, it was identified that Compound 16 among the compound of formula (I) according to the present invention exhibits a very strong inhibition of gastric juice secretion and a high acidity lowering effect. Meanwhile, Compound 2 is characterized by the fact that it can be very easily synthesized in high yield, although its anti-ulcer effect is similar to that of Omeprazole.

For reference, $ED_{50}$ values of Compounds 2 and 16 and Omeprazole are described in the following Table 6.

TABLE 6

| | Inhibition of gastric juice secretion $ED_{50}$ (mg/kg) | Inhibition of acidity $ED_{50}$ (mg/kg) |
|---|---|---|
| Compound 2 | 8.18 | 4.04 |
| Compound 16 | 4.53 | 1.85 |
| Omeprazole | 8.50 | 3.73 |

TEST 3 : Acute toxicity test

Five weeks aged ICR (male, female) mouse were pre-bred in the breeding cage for one week and then the animals showing a smooth gain in body weight were randomly selected and used in this test. The amount to be administered to the test animals was established on the basis of the maximum dose of 5,000 mg/kg with the common ratio of 1.5.

The test compounds in a powder were suspended in 0.5% methylcellulose and administered per oral using a 1ml syringe. The other specific conditions for administration are described in the following.

| Class | | | | | |
|---|---|---|---|---|---|
| Group | Sex | Number of animals | Total dose (mg/kg) | Number of dosage per day | Dose (mg/kg) | Duration of dosage (days) |
| Control | M | 5 | | 1 | 30 | 14 |
| | F | 5 | | 1 | 30 | 14 |
| G1 | M | 5 | 987 | 1 | 30 | 14 |
| | F | 5 | 987 | 1 | 30 | 14 |
| G2 | M | 5 | 1,481 | 1 | 30 | 14 |
| | F | 5 | 1,481 | 1 | 30 | 14 |
| G3 | M | 5 | 2,222 | 1 | 30 | 14 |
| | F | 5 | 2,222 | 1 | 30 | 14 |
| G4 | M | 5 | 3,333 | 1 | 30 | 14 |
| | F | 5 | 3,333 | 1 | 30 | 14 |
| G5 | M | 5 | 5,000 | 1 | 30 | 14 |
| | F | 5 | 5,000 | 1 | 30 | 14 |

In the above test, the control group received only 0.5% methylcellulose.

1) Test items (1) Clinical symptoms and death of test animals

The clinical symptoms and death of test animals caused by the test compounds were recorded immediately after administration of the test compounds and during the overall test period.

(2) Change in body weight

The change in body weight was recorded three times, i.e. on the day of administration, one week after administration and the end day of test.

(3) Autopsy view

After the test is completed, all the test animals were sacrificed with ether and the change in the internal and external organs due to the test compounds was observed.

2) Test results (1) Clinical symptoms and death of test animals

No specific abnormal clinical symptoms were observed in all male and female rats of the Compound 2 group and the Omeprazole group at the maximum administration amount of 5,000 mg per kg of body weight.

(2) Change in body weight

In comparison with the control group (0.5% CMC group), no significant change in body weight caused by the test compound was observed in the test animals. The change in body weight in the test animals are described in the following Tables 7-1 and 7-2.

(3) Visual autopsy view

No specific abnormal autopsy view was observed in survived animals in the Compound 2 group and the Omeprazole group.

Conclusion

To evaluate the safety of Compound 2 the oral acute toxicity of Compound 2 was determined using Omeprazole as the control compound in ICR male and female mouse. The results are as follows:

(1) In view of clinical symptoms, death and autopsy results, the acute toxicity of Compound 2 is very low as in Omeprazole.

(2) It could be estimated that the $LD_{50}$ values of Compound 2 and Omeprazole is greater than 5,000 mg/kg of body weight.

(3) From the result of acute toxicity test, it could be identified that Compound 2 is a very safe compound.

The $LD_{50}$ values of Compound 2 and Omeprazole as determined according to the above oral acute toxicity test in mouse are described in the following table.

| Sex | Test compound | |
|---|---|---|
| | Compound 2 (mg/kg BW) | Omeprazole (mg/kg BW) |
| Male | 5,000.0 < | 5,000.0 < |
| Female | 5,000.0 < | 5,000.0 < |

TABLE 6-1

Lethality and $LD_{50}$ of Omeprazole

| Sex | Dose (mg/kg) | 0 | 1 | 2 | 3 | 4 | 5 | 6 | 7 | 8 | 9 | 10 | 11 | 12 | 13 | 14 | Lethality | $LD_{50}$ (mg/kg) |
|---|---|---|---|---|---|---|---|---|---|---|---|---|---|---|---|---|---|---|
| Male | 0 | 0 | 0 | 0 | 0 | 0 | 0 | 0 | 0 | 0 | 0 | 0 | 0 | 0 | 0 | 0 | 0/5 | 5000.0 < |
| | 987 | 0 | 0 | 0 | 0 | 0 | 0 | 0 | 0 | 0 | 0 | 0 | 0 | 0 | 0 | 0 | 0/5 | |
| | 1481 | 0 | 0 | 0 | 0 | 0 | 0 | 0 | 0 | 0 | 0 | 0 | 0 | 0 | 0 | 0 | 0/5 | |
| | 2222 | 0 | 0 | 0 | 0 | 0 | 0 | 0 | 0 | 0 | 0 | 0 | 0 | 0 | 0 | 0 | 0/5 | |
| | 3333 | 0 | 0 | 0 | 0 | 0 | 0 | 0 | 0 | 0 | 0 | 0 | 0 | 0 | 0 | 0 | 0/5 | |
| | 5000 | 0 | 0 | 0 | 0 | 0 | 0 | 0 | 0 | 0 | 0 | 0 | 0 | 0 | 0 | 0 | 0/5 | |
| Female | 0 | 0 | 0 | 0 | 0 | 0 | 0 | 0 | 0 | 0 | 0 | 0 | 0 | 0 | 0 | 0 | 0/5 | 5000.0 < |
| | 987 | 0 | 0 | 0 | 0 | 0 | 0 | 0 | 0 | 0 | 0 | 0 | 0 | 0 | 0 | 0 | 0/5 | |
| | 1481 | 0 | 0 | 0 | 0 | 0 | 0 | 0 | 0 | 0 | 0 | 0 | 0 | 0 | 0 | 0 | 0/5 | |
| | 2222 | 0 | 0 | 0 | 0 | 0 | 0 | 0 | 0 | 0 | 0 | 0 | 0 | 0 | 0 | 0 | 0/5 | |
| | 3333 | 0 | 0 | 0 | 0 | 0 | 0 | 0 | 0 | 0 | 0 | 0 | 0 | 0 | 0 | 0 | 0/5 | |
| | 5000 | 0 | 0 | 0 | 0 | 0 | 0 | 0 | 0 | 0 | 0 | 0 | 0 | 0 | 0 | 0 | 0/5 | |

TABLE 6-2

Lethality and $LD_{50}$ of Omeprazole

| Sex | Dose (mg/kg) | 0 | 1 | 2 | 3 | 4 | 5 | 6 | 7 | 8 | 9 | 10 | 11 | 12 | 13 | 14 | Lethality | $LD_{50}$ (mg/kg) |
|---|---|---|---|---|---|---|---|---|---|---|---|---|---|---|---|---|---|---|
| Male | 0 | 0 | 0 | 0 | 0 | 0 | 0 | 0 | 0 | 0 | 0 | 0 | 0 | 0 | 0 | 0 | 0/5 | 5000.0 < |
| | 987 | 0 | 0 | 0 | 0 | 0 | 0 | 0 | 0 | 0 | 0 | 0 | 0 | 0 | 0 | 0 | 0/5 | |
| | 1481 | 0 | 0 | 0 | 0 | 0 | 0 | 0 | 0 | 0 | 0 | 0 | 0 | 0 | 0 | 0 | 0/5 | |
| | 2222 | 0 | 0 | 0 | 0 | 0 | 0 | 0 | 0 | 0 | 0 | 0 | 0 | 0 | 0 | 0 | 0/5 | |
| | 3333 | 0 | 0 | 0 | 0 | 0 | 0 | 0 | 0 | 0 | 0 | 0 | 0 | 0 | 0 | 0 | 0/5 | |
| | 5000 | 0 | 0 | 0 | 0 | 0 | 0 | 0 | 0 | 0 | 0 | 0 | 0 | 0 | 0 | 0 | 0/5 | |
| Female | 0 | 0 | 0 | 0 | 0 | 0 | 0 | 0 | 0 | 0 | 0 | 0 | 0 | 0 | 0 | 0 | 0/5 | 5000.0 < |
| | 987 | 0 | 0 | 0 | 0 | 0 | 0 | 0 | 0 | 0 | 0 | 0 | 0 | 0 | 0 | 0 | 0/5 | |
| | 1481 | 0 | 0 | 0 | 0 | 0 | 0 | 0 | 0 | 0 | 0 | 0 | 0 | 0 | 0 | 0 | 0/5 | |
| | 2222 | 0 | 0 | 0 | 0 | 0 | 0 | 0 | 0 | 0 | 0 | 0 | 0 | 0 | 0 | 0 | 0/5 | |
| | 3333 | 0 | 0 | 0 | 0 | 0 | 0 | 0 | 0 | 0 | 0 | 0 | 0 | 0 | 0 | 0 | 0/5 | |
| | 5000 | 0 | 0 | 0 | 0 | 0 | 0 | 0 | 0 | 0 | 0 | 0 | 0 | 0 | 0 | 0 | 0/5 | |

TABLE 7-1

Change in body weight after administration of Omeprazole

| Sex | Day | 5000 | 3333 | 2222 | 1481 | 987 | 0 |
|---|---|---|---|---|---|---|---|
| Male | 0 | 24.56 ± 1.35 | 24.51 ± 1.43 | 24.52 ± 1.64 | 24.86 ± 0.89 | 24.78 ± 1.42 | 24.85 ± 1.56 |
|  | 1 | 26.55 ± 2.12 | 25.89 ± 2.54 | 25.89 ± 1.54 | 26.55 ± 1.54 | 26.54 ± 1.86 | 26.54 ± 1.86 |
|  | 4 | 26.12 ± 2.56 | 26.56 ± 2.85 | 26.56 ± 2.54 | 27.41 ± 2.11 | 27.15 ± 2.65 | 27.37 ± 2.34 |
|  | 7 | 27.35 ± 3.21 | 28.56 ± 3.45 | 27.57 ± 3.54 | 28.49 ± 3.56 | 28.86 ± 1.54 | 28.87 ± 3.41 |
|  | 10 | 28.25 ± 2.55 | 29.41 ± 3.95 | 27.85 ± 4.51 | 28.15 ± 3.14 | 28.95 ± 2.54 | 28.87 ± 3.55 |
|  | 14 | 28.45 ± 3.56 | 29.56 ± 4.23 | 28.55 ± 4.65 | 28.85 ± 3.41 | 29.16 ± 2.35 | 29.42 ± 3.68 |
| Female | 0 | 21.70 ± 0.85 | 21.14 ± 0.69 | 21.56 ± 1.55 | 21.89 ± 1.45 | 21.35 ± 1.75 | 21.64 ± 1.05 |
|  | 1 | 22.56 ± 1.56 | 21.65 ± 1.78 | 22.09 ± 1.54 | 21.95 ± 2.05 | 21.85 ± 1.54 | 22.45 ± 1.85 |
|  | 4 | 23.49 ± 1.95 | 22.95 ± 1.62 | 22.95 ± 2.05 | 22.55 ± 1.89 | 23.24 ± 1.97 | 23.54 ± 1.75 |
|  | 7 | 24.97 ± 1.55 | 23.85 ± 2.14 | 23.59 ± 1.85 | 23.58 ± 1.95 | 24.16 ± 2.52 | 24.52 ± 1.95 |
|  | 10 | 25.35 ± 2.01 | 24.42 ± 2.57 | 25.48 ± 2.18 | 25.87 ± 2.45 | 25.54 ± 2.25 | 25.14 ± 2.51 |
|  | 14 | 26.55 ± 2.54 | 25.89 ± 2.45 | 26.75 ± 2.54 | 26.21 ± 2.54 | 26.74 ± 2.78 | 26.54 ± 2.57 |

TABLE 7-2

Change in body weight after administration of Compound 2

| Sex | Day | 5000 | 3333 | 2222 | 1481 | 987 | 0 |
|---|---|---|---|---|---|---|---|
| Male | 0 | 24.97 ± 1.26 | 24.40 ± 1.39 | 24.42 ± 1.33 | 24.92 ± 0.97 | 24.81 ± 1.05 | 24.74 ± 1.27 |
|  | 1 | 26.75 ± 2.08 | 25.97 ± 2.73 | 25.80 ± 2.50 | 26.98 ± 1.49 | 26.70 ± 1.66 | 26.60 ± 1.91 |
|  | 4 | 26.07 ± 2.67 | 26.32 ± 2.67 | 26.07 ± 3.03 | 27.31 ± 2.42 | 27.11 ± 2.18 | 27.02 ± 2.71 |
|  | 7 | 27.31 ± 3.07 | 28.95 ± 3.65 | 27.27 ± 3.93 | 28.25 ± 3.81 | 28.28 ± 1.97 | 28.14 ± 3.55 |
|  | 10 | 28.05 ± 2.96 | 29.91 ± 3.96 | 27.52 ± 4.30 | 28.95 ± 3.65 | 28.37 ± 2.00 | 28.41 ± 4.28 |
|  | 14 | 28.45 ± 3.25 | 29.54 ± 4.23 | 28.57 ± 4.63 | 28.52 ± 3.96 | 28.80 ± 2.47 | 28.88 ± 4.85 |
| Female | 0 | 21.51 ± 0.95 | 21.21 ± 0.92 | 21.44 ± 1.02 | 21.05 ± 0.83 | 21.24 ± 1.09 | 21.67 ± 1.05 |
|  | 1 | 22.30 ± 1.45 | 21.50 ± 1.04 | 22.08 ± 1.13 | 21.47 ± 0.59 | 21.91 ± 1.37 | 22.11 ± 0.81 |
|  | 4 | 23.98 ± 1.92 | 22.82 ± 1.88 | 22.84 ± 1.86 | 22.18 ± 1.46 | 23.58 ± 1.89 | 23.58 ± 1.58 |
|  | 7 | 24.45 ± 1.68 | 23.21 ± 1.80 | 23.89 ± 1.67 | 23.21 ± 1.65 | 24.23 ± 2.10 | 24.34 ± 1.80 |
|  | 10 | 25.57 ± 2.05 | 24.35 ± 2.66 | 25.45 ± 2.34 | 25.67 ± 1.85 | 25.45 ± 2.45 | 25.16 ± 2.32 |
|  | 14 | 26.48 ± 2.25 | 25.56 ± 2.37 | 26.64 ± 2.55 | 26.35 ± 2.30 | 26.54 ± 2.66 | 26.28 ± 2.44 |

Although this invention has been described in its preferred form with a certain degree of particularity, it is appreciated by those skilled in the art that the present disclosure of the preferred form has been made only by way of example and that numerous changes in the details of the construction, combination and arrangement of parts may be made without departing from the spirit and scope of the invention.

What is claimed is:

1. A compound having the following formula (I):

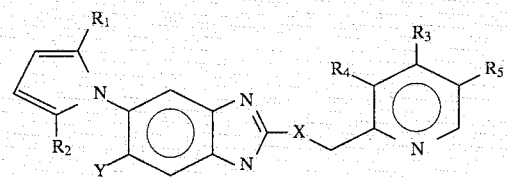

or a pharmaceutically acceptable salt thereof, in which

X represents S, SO or $SO_2$,

Y represents halogen, $R_1$ and $R_2$ independently from each other represent hydrogen or methyl, $R_3$ represents hydrogen, $C_1$–$C_8$ alkyl, —$SR_6$, —$N(R_7)_2$, [1-piperidinyl, 4-morpholinyl, 4-methylpiperazin-1-yl, 1-pyrrolidinyl] or a group of formula —$OR_6$ or —$O(CH_2)_m$—Z, wherein $R_6$ represents $C_1$–$C_4$ alkyl, $C_2$–$C_4$ alkenyl, [optionally substituted] $C_3$–$C_{10}$ cycloalkyl optionally substituted with $C_1$–$C_4$ alkyl, $C_2$–$C_5$ fluoroalkyl, phenyl optionally substituted with $C_1$–$C_4$ alkyl or benzyl optionally substituted with $C_1$–$C_4$ alkyl, $R_7$ represents hydrogen or $C_1$–$C_5$ alkyl, Z represents a group of formula, wherein q denotes an integer of 1 to 3, and $R_9$ represents hydrogen, m represents an integer of 2 to 10, and $R_4$ and $R_5$ independently from each other represent hydrogen, lower alkoxy or $C_1$–$C_5$ alkyl.

2. The compound of formula (I) as defined in claim 1, wherein

X represents S, SO, or $SO_2$,

Y represents fluoro, $R_1$ and $R_2$ independently from each other represent hydrogen or methyl, $R_3$ represents hydrogen, methyl, methoxy, ethoxy, ethoxyethoxy, 2,2,2-trifluoroethoxy, 3,3,3,2,2-pentafluoropropxy or 4,4,4,3,3,2,2-heptafluorobutoxy, $R_4$ represents hydrogen, methyl or methoxy, and $R_5$ represents hydrogen, methyl or ethyl.

3. The compound of formula (I) as defined in claim 2, wherein

X represents SO,

Y represents fluoro, $R_1$ and $R_2$ independently from each other represent hydrogen or methyl, $R_3$ represents methoxy or ethoxy, and $R_4$ and $R_5$ independently from each other represent hydrogen, methyl or ethyl.

4. An anti-ulcer composition comprising an effective amount of a compound having the following formula (I):

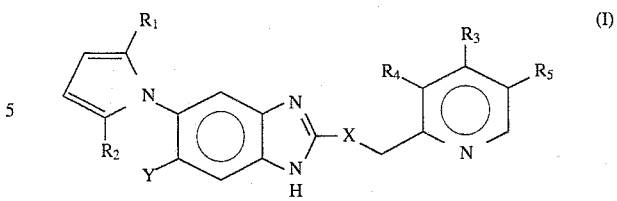

in which X, Y, $R_1$, $R_2$, $R_3$, $R_4$, and $R_5$ are defined as described in claim 1, or pharmaceutically acceptable salt thereof as an active ingredient together with a pharmaceutically acceptable carrier, adjuvant or excipient therefor.

* * * * *

UNITED STATES PATENT AND TRADEMARK OFFICE
CERTIFICATE OF CORRECTION

PATENT NO. : 5,554,631
DATED : September 10, 1996
INVENTOR(S) : Su Ung KIM et al.

It is certified that error appears in the above-identified patent and that said Letters Patent is hereby corrected as shown below:

On the title page, item [30] should read as follows:

--[30]  Foreign Application Priority Data
   Dec. 2, 1994   [KR] Rep. of Korea . . . . 94-32612--

Signed and Sealed this

Eighteenth Day of March, 1997

Attest:

BRUCE LEHMAN

*Attesting Officer*       *Commissioner of Patents and Trademarks*